(12) United States Patent
Braga et al.

(10) Patent No.: US 10,178,877 B2
(45) Date of Patent: Jan. 15, 2019

(54) COFFEE OIL CAPSULES

(71) Applicant: NESTEC S.A., Vevey (CH)

(72) Inventors: Ana Luiza Braga, Intermares-Cabedelo-Paraiba (BR); Zeynel Deniz Gunes, Lausanne (CH); Joeska Husny, Bern (CH); Daniel Andre Pretre, Chardonne (CH); Elodie Soussan, Bern (CH)

(73) Assignee: Nestec S.A., Vevey (CH)

( * ) Notice: Subject to any disclaimer, the term of this patent is extended or adjusted under 35 U.S.C. 154(b) by 31 days.

(21) Appl. No.: 14/787,820

(22) PCT Filed: May 12, 2014

(86) PCT No.: PCT/EP2014/059621
§ 371 (c)(1),
(2) Date: Oct. 29, 2015

(87) PCT Pub. No.: WO2014/184129
PCT Pub. Date: Nov. 20, 2014

(65) Prior Publication Data
US 2016/0113314 A1   Apr. 28, 2016

(30) Foreign Application Priority Data
May 13, 2013 (EP) .................................. 13167415

(51) Int. Cl.
| | |
|---|---|
| A23P 10/35 | (2016.01) |
| A23F 5/46 | (2006.01) |
| A61K 36/74 | (2006.01) |
| A61Q 19/00 | (2006.01) |
| A61K 8/92 | (2006.01) |
| A61K 8/97 | (2017.01) |
| A61K 8/11 | (2006.01) |
| A23L 27/00 | (2016.01) |
| A23L 27/28 | (2016.01) |

(52) U.S. Cl.
CPC ............... *A23P 10/35* (2016.08); *A23F 5/46* (2013.01); *A23L 27/28* (2016.08); *A23L 27/72* (2016.08); *A61K 8/11* (2013.01); *A61K 8/922* (2013.01); *A61K 8/97* (2013.01); *A61K 36/74* (2013.01); *A61Q 19/00* (2013.01); *A23V 2002/00* (2013.01); *A61K 2236/00* (2013.01); *A61K 2800/412* (2013.01)

(58) Field of Classification Search
None
See application file for complete search history.

(56) References Cited

U.S. PATENT DOCUMENTS

| | | | |
|---|---|---|---|
| 4,820,543 A | 4/1989 | Osawa | |
| 5,399,368 A | 3/1995 | Garwood et al. | |
| 6,319,537 B1 * | 11/2001 | Cheng | A23F 5/243 426/119 |
| 2003/0091696 A1 | 5/2003 | Panesar | |
| 2007/0259084 A1 | 11/2007 | Gaonkar et al. | |
| 2010/0316784 A1 * | 12/2010 | Tonyes | A23F 5/18 426/594 |

FOREIGN PATENT DOCUMENTS

| | | | |
|---|---|---|---|
| EP | 0 008 015 | * | 2/1980 |
| EP | 0008015 | | 2/1980 |
| EP | 0815743 | | 1/1998 |
| FR | 2811203 A1 | | 1/2002 |
| JP | S5898041 A | | 6/1983 |
| JP | 02-203749 A | | 8/1990 |
| JP | 2016-521132 A | | 7/2016 |
| RU | 2286064 C2 | | 10/2006 |
| WO | 9623423 | | 8/1996 |
| WO | WO-96/23423 | * | 8/1996 |

OTHER PUBLICATIONS

Teo et al. "Effect of pH on Physicochemical Properties and Encapsulation Efficiency of PEGylated Linolenic Acid Vesicles" E-Journal of Chemistry, 2012, vol. 9, No. 2, pp. 729-738.
Siow et al. "Effect of pH on Garlic Oil Encapsulation by Complex Coacervation" J. Food Process Technol., 2013, vol. 4, No. 1, 5 pages.
Japanese Office Action for corresponding application P2016-513315, Dispatch No. 149750, Dispatch Date Apr. 10, 2018, 10 pages.
Russian Office Action for corresponding application 2015153421/13(082389), dated Mar. 13, 2018, 6 pages.

* cited by examiner

*Primary Examiner* — Celeste A Roney
(74) *Attorney, Agent, or Firm* — K&L Gates LLP

(57) ABSTRACT

The present invention relates to a process for producing capsules comprising a composition comprising coffee oil. The invention also relates to capsules obtainable by such process. In addition the invention relates to compositions, food ingredients and food products comprising such capsules.

20 Claims, 10 Drawing Sheets

A

B

| Intact capsules | Start bursting | All 80 μm caps. burst<br>10 μm caps. still intact | All capsules burst |

| | 0.5% | 1.5% | 2.5% | 3.5% | 5.0% |
|---|---|---|---|---|---|
| After production | | | | | |
| Capsules in Heavy Liquor | N/A | | | | N/A |

Fig. 4

| 2.5% WPI pH 9 / GRAB oil | 1% Na-caseinate pH7 / GRAB oil | 1% Chlorogenic acid pH 9/ GRAB oil | 1% Chlorogenic acid pH 7/ GRAB oil |
|---|---|---|---|
|  |  |  |  |

COFFEE OIL CAPSULES

CROSS REFERENCE TO RELATED APPLICATIONS

The present application is a National Stage of International Application No. PCT/EP2014/059621, filed on May 12, 2014, which claims priority to European Patent Application No. 13167415.2, filed on May 13, 2013, the entire contents of which are being incorporated herein by reference.

TECHNICAL FIELD OF THE INVENTION

The present invention relates to capsules comprising coffee oil as an aroma delivery system. In particular the present invention relates to processes for producing such coffee oil capsules. The invention furthermore relates to food ingredients and food products comprising such coffee oil capsules.

BACKGROUND OF THE INVENTION

Coffee aroma volatiles are released very fast when pure soluble coffee (PSC) is reconstituted in hot water, resulting in fast decrease of the above-cup aroma perception of coffee flavour by the consumers. One approach to control coffee aroma release is the addition of aroma delivery systems during the coffee process, so that they are embedded in the coffee powder. An aroma delivery system can be composed of oil droplets each surrounded by a membrane. However, there is an increasing demand from consumers that coffee products are constituted entirely from coffee beans.

Hence, an improved system for delivery of aromas would be advantageous, and in particular a more efficient and/or reliable aroma delivery system constituted entirely of coffee derived materials would be advantageous.

SUMMARY OF THE INVENTION

The present invention relates to the formation of coffee oil capsules made of materials completely or primarily from coffee beans. Thus, an object of the present invention relates to the provision of encapsulated compositions comprising coffee oil for use as an aroma release system.

In particular, it is an object of the present invention to provide an aroma release system that solves the above mentioned problems of the prior art with aroma release systems composed entirely of coffee constituents.

Thus, one aspect of the invention relates to a process for producing a capsule comprising coffee oil, the process comprising
a) providing
   one or more aqueous compositions comprising coffee extract, and
   a composition comprising coffee oil;
b) optionally, emulsifying the composition comprising coffee oil with an aqueous phase, providing an oil-in-water emulsion;
c) mixing a first aqueous composition comprising coffee extract with the composition comprising coffee oil at a pH below 7, thereby providing an oil-in-water emulsion;
d) raising the pH to 7 or above;
e) optionally, concentrating the oil-in-water emulsion;
f) optionally, mixing the oil-in-water emulsion with concentrated coffee extract;
g) optionally, drying the oil-in-water emulsion; and
h) providing the capsule comprising a composition comprising coffee oil.

Another aspect of the present invention relates to a capsule comprising coffee oil obtainable by a process according to the process of the invention.

Yet another aspect of the present invention is to provide a capsule comprising coffee oil, the capsule comprising
   a core of a composition comprising coffee oil; and
   a membrane surrounding the core, wherein the membrane comprises coffee oil constituents linked with aqueous coffee extract constituents.

Still another aspect of the present invention is to provide a composition comprising coffee oil capsules according to the invention.

A further aspect according to the present invention relates to a food or non-food matrix comprising a capsule comprising coffee oil according to the present invention.

Yet a further aspect relates to a food product comprising a food ingredient or composition according to the invention.

An additional aspect relates to the use of a composition comprising coffee oil or derivatives thereof for the production of capsules comprising coffee oil.

BRIEF DESCRIPTION OF THE FIGURES

FIG. 4 shows microscopy pictures of green coffee oil capsules pH 7, produced with several extract concentration (final pH 7). Top line: After production. Lower line: In 50% concentrated coffee extract.

Figure 1:
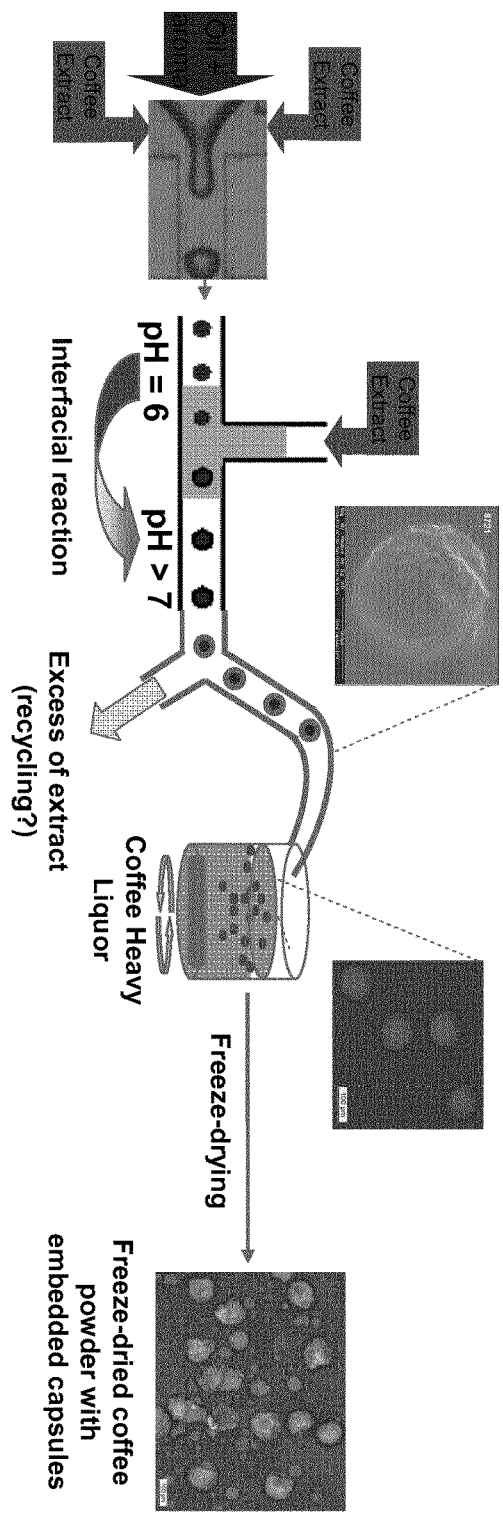
FIG. 1 shows a schematic overview of the production process.

The present invention will now be described in more detail in the following.

DETAILED DESCRIPTION OF THE INVENTION

As mentioned above the invention relates to processes for producing encapsulated coffee oils, which may confer controlled/postponed release of aromas. Preferably the entire capsule and its content are derived from coffee. Although described herein as a system for encapsulation and release of aromas, it is to be understood that the system can also be used for encapsulation and release of other compounds, e.g. nutritional compounds such as vitamins.

Process for Producing a Capsule Comprising Coffee Oil

An aspect of the present invention relates to a process for producing a capsule comprising coffee oil, the process comprising
a) providing
one or more aqueous compositions comprising coffee extract, and
a composition comprising coffee oil;
b) optionally, emulsifying the composition comprising coffee oil with an aqueous phase, providing an oil-in-water emulsion;
c) mixing a first aqueous composition comprising coffee extract with the composition comprising coffee oil at a pH below 7, thereby providing an oil-in-water emulsion;
d) raising the pH to 7 or above;
e) optionally, concentrating the oil-in-water emulsion;
f) optionally, mixing the oil-in-water emulsion with coffee concentrated extract;
g) optionally, drying the oil-in-water emulsion; and
h) providing the capsule comprising a composition comprising coffee oil.

In the present context the term "capsule comprising coffee oil" or "coffee oil capsule" relates to a composition comprising coffee oil which is protected from the surrounding environment by a membrane. In a preferred embodiment the membrane comprises constituents derived from coffee extract (aqueous) and coffee oil. Thus, the membrane is a degradable organic food grade membrane.

It is to be understood that coffee oil may also be first emulsified by mixing with an aqueous phase that does not comprise coffee extract, where droplets will be formed, then suitable coffee extract is added to create the non-solidified membrane, which may then be solidified at a pH of 7.0 or higher. This is illustrated by optional step b).

The mixing in step c) is performed at a pH below 7. In an embodiment step c) is performed at a pH in the range 4.0-6.5, such as in the range 5.0-6.4, such as in the range 5.5-6.2.

Step d) is introduced to further strengthen/solidify the formed membrane by raising the pH to 7 or above. Thus, in an embodiment the pH during step d) is raised to 7 or above by the addition of a second aqueous composition comprising coffee extract. By using coffee extract to raise the pH it is ensured that all components used to raise the pH is derived entirely of coffee constituents.

In the present context the term "coffee extract" or "aqueous coffee extract" refers to an extract obtained from coffee beans. An extract may be obtained by filtration of a whole coffee bean extract by first microfiltration (e.g. 0.2 µm filter) and subsequently filtering the retentate by ultrafiltration (e.g. 30 kDa filter). The obtained retentate normally has a dry matter content (w/w) in the range 10-40%, which can then be diluted or concentrated into an appropriate concentration.

In general the coffee extract may be a mixture of extracts to optimize the flavour composition. However, it may also be desirable to perform the complete process with extracts obtained from the same source. Thus, in an embodiment the first and the second aqueous composition comprising coffee extract is obtained from the same source.

To improve formation of the encapsulated oils, it may be advantageous to remove certain components from the coffee extract. Thus, in an embodiment the aqueous compositions comprising coffee extract is substantially free or free of citrate and/or acetic compounds. Thus, in an embodiment the dry matter content of citrate is in the range 0.001-1% by weight, such as in the range 0.001-0.5% such as in the range 0.01-0.5%, or such as in the range 0.01-0.05%. In yet an embodiment the combined dry matter content of acetic compounds is in the range 0-1% by weight, such as in the range 0-0.5% such as in the range 0.01-0.5%, or such as in the range 0.01-0.05%. As shown in examples 2 and 11 the presence of citrate impairs membrane formation and it may therefore be advantageous to remove e.g. citrate from the coffee extract.

In the present context the term "dry matter content" refers to the amount by weight of solids in a composition. Thus "dry matter" is weight of the constituents excluding water. The dry matter content of a component in a composition is described as the percentage of the component relative to the total weight of dry matter in the composition. Thus, in the present context the dry matter content of a component may be described as 40% (w/w) if 40% of the weight of the dry matter is constituted of the specific component. In the present context it is to be understood that oil is part of the dry matter content.

The coffee extract may be obtained from different types of coffee to optimize the flavour composition. Thus, in an embodiment the aqueous coffee extract is provided from the group consisting of green coffee, toasted coffee, and/or roasted coffee. The coffee extract may be obtained by different filtration steps. Thus, in an embodiment the aqueous coffee extract is obtained by micro-filtration and/or ultra-filtration.

It may be possible to control the strength of the membrane by controlling parameters of the input material. Thus, in an embodiment the aqueous composition comprising coffee extract provided in step c), has a dry matter content by weight (w/w) of coffee extract in the range 0.1-50%, such as in the range 0.1-30%, such as in the range 0.1-20%, such as in the range 0.3-10%, such as in the range 0.3-5%, such as in the range 1-5% such as in the range 2-5%, such as in the range 2-3%, or such as around 2.5%. As shown in Example 4, the strength of membrane can be controlled by varying the dry matter content of coffee extract in step c).

In the present context the term "coffee oil" refers to oils obtained from coffee. Example 1 describes how coffee oil may be obtained. Example 1 furthermore shows the typical components of whole coffee oil.

It may be possible to improve the aroma release from the encapsulated coffee. Thus, in an embodiment the composition comprising the coffee oil further comprises aroma constituents. By loading/premixing the coffee oil with aroma constituents before forming the encapsulated composition comprising coffee oil an improved and/or increased aroma release may be formed. As previously mentioned the aromas should preferably be derived from coffee beans. Thus, in an embodiment the aroma constituents comprise coffee aromas obtained from coffee beans. In yet an embodiment the coffee aroma constituents are obtained from green coffee, toasted coffee and/or roasted coffee.

The amount of coffee oil in the composition comprising coffee oil may also influence the ability control the encapsulation step. Thus, in an embodiment the composition comprising coffee oil provided in step c) comprises at least 5% coffee oil by weight (w/w), such as at least 10% such as at least 20%, such as at least 30%, such as at least 40%, such as at least 60%, such as at least 80%, such as at least 90% or such as 100%. A shown in Example 9 when using a source of crude coffee oil at least 40% coffee oil is required to initiate the capsule formation, however the capsules can form even for a coffee oil fraction as low as 5%. It is noted that capsule formation was not initiated when using other types of oils. Thus, coffee oil comprises constituents required for capsule formation.

It may also be possible to identify fractions of coffee oil which is able to initiate the encapsulation step. Thus in an embodiment the coffee oil is a fraction of whole coffee oil. In yet an embodiment the fraction of coffee oil is an oil sediment fraction. As shown in example 10 a coffee oil sediment fraction is also able to initiate encapsulation whereas the supernatant fraction was less efficient (data not shown). Thus, the constituents responsible for capsule formation appear to be dominantly present in the sediment fraction.

The oil sediment fraction may be obtained by different methods. In an embodiment the oil sediment is obtained by centrifugation of crude coffee oil. As an example a centrifugation process could be 50,000 g (g being the earth gravity acceleration) for two hours to separate the crude oil sediment and the supernatant. In yet an embodiment the process includes separating the oil into a supernatant and a sediment phase. In yet an embodiment the composition comprising coffee oil provided in step c) comprises at least 0.01% coffee oil sediment, such as at least 0.1% coffee oil sediment, such as at least 1% by weight of coffee oil sediment, such as in the range 1-20%, such as in the range 1-15%, such as in the range 1-10%, such as in the range 3-20%, such as in the range 5-20%, such as in the range 10-20%.

Overall it is to be understood that either coffee oil and/or coffee oil sediment may preferably be used in the process according to the invention.

In yet an embodiment the coffee oil is obtained from the group consisting of green coffee, toasted coffee, roasted coffee, extracted green coffee, extracted toasted coffee and/or extracted roasted coffee.

In a specific embodiment the mixing step c) results in a mixture having a dry matter content by weight (w/w) of coffee extract in the range 1-10% and coffee oil in the range 3-60% (w/w), such as coffee extract in the range 1-5% and coffee oil in the range 5% (w/w), such as coffee extract in the range 1-5% and coffee oil in the range 10-60%, or such as coffee extract in the range 1-5% and coffee oil in the range 10-50%.

In another specific embodiment the mixing step c) results in a mixture having a dry matter content by weight (w/w) of coffee extract in the range 1-10% and coffee oil sediment in the range 0.1-20% (w/w), such as coffee extract in the range 1-5% and coffee oil sediment in the range 1-20%, such as coffee extract in the range 1-5% and coffee oil sediment in the range 1-10%, or coffee extract in the range 1-5% and coffee oil sediment in the range 1-5% (w/w).

Surfactants, defined here as molecules or particles that have an affinity for oil-water interfaces, may improve the formation of the capsules. Thus, in an embodiment the coffee oil is enriched in surfactants. In yet an embodiment the surfactants are obtained from coffee. In yet another embodiment the surfactants are selected from the group consisting of proteins, and/or polyphenols, and/or polysaccharides.

In the present context "concentrated coffee extract" or "coffee heavy liquor" refers to a coffee extract having a dry mater content of 5% or above, such as above 25%, such as above 40%, such as in the range 40-70% or such as 50-70%.

Furthermore, the pH of concentrated coffee extract is normally higher than in coffee extracts with lower dry matter content since acidic components are removed during the concentration process (e.g. evaporation). Thus, concentrated coffee extract may have a pH in the range 6-12. An advantage of the concentration is that the concentrated coffee extract has a lower content of acidic compounds, which, as shown in e.g. example 11, may improve capsule formation. When coffee extract is used in step d) to raise the pH to above 7, it is to be understood that a coffee extract with a pH above 7 is used, such as with a pH in the range 8-12. The pH may be decreased after capsule formation for use of the capsules according to specific applications. The preferred target range of the final pH is 5.0 to 8.0.

The dry matter content of the concentrated coffee extract may vary. In an embodiment the concentrated coffee extract has a dry matter content of 5% or above, such as above 25%, such as above 40%, such as in the range 40-70% or such as 50-70%.

In yet an embodiment the coffee extract (e.g. concentrated coffee extract) in step f) is provided by evaporation or filtration of part of an aqueous coffee extract. In a further embodiment the concentration step e) is performed by gravitational forces such as centrifugation e.g. decantation or centrifugation.

In a further embodiment the emulsion is monodisperse.

As mentioned above the encapsulated composition is preferably derived from coffee. Thus, in an embodiment 0.1-100% of the dry matter content (w/w) of the coffee oil capsule is derived from coffee beans, such as 1-100%, such as 5-100%, such as 10-100%, such as 25-100%, such as 50-100% of the dry matter content (w/w) of the coffee oil capsule is derived from coffee beans, such as 70-100%, such as 80-100%, such as 90-100% such as 95-100%, such as 100%. In a further embodiment 40-100% of the oils are derived from coffee such as 70-100%, such as 80-100%, such as 90-100% such as 95-100%, such as 100%. As previously mentioned preferably the complete capsule is derived from coffee beans.

The mixing in step c) may be performed by different means. Thus, in an embodiment the mixing in step c) is performed in a microfluidic device, by a parallelized (i.e. containing many emulsion generating geometry parts) microfluidic device, by a static membrane emulsification device, by a rotating membrane emulsification device, or in a classic shear mixing system or rotor-stator type device. By the denomination "microfluidic chip", it is understood to include all drop generator devices with a characteristic dimension controlling the drop size (pore size, channel diameter) comprised e.g. between 1 micron and 2 millimeters.

The provided encapsulated composition comprising coffee oil may subsequently be dried. Thus, in an embodiment the drying in step g) is performed by freeze-drying, spray-drying and/or conventional water evaporation process.

The coffee oil capsule (capsule comprising coffee oil) according to the present invention has some distinct properties. Thus, an aspect of the present invention relates to a capsule comprising coffee oil obtainable by a process according to the process of the invention. In the example section unique features of the capsules according to the invention are described.

Capsule Comprising Coffee Oil

The capsule comprising coffee oil (coffee oil capsule) obtainable by the process according to the present invention comprises a unique encapsulation membrane protecting against early release of aroma constituents. The encapsulation membrane comprises components derived both from the aqueous composition and the oil composition. Thus, an aspect of the present invention relates to a capsule comprising coffee oil, the capsule comprising a core of a composition comprising coffee oil; and a membrane surrounding the core, wherein the membrane comprises coffee oil constituents and aqueous coffee extract constituents.

In a preferred embodiment, the membrane comprises at least 1% of coffee oil constituents and at least 1% aqueous coffee extract constituents.

The constituents derived from the aqueous coffee extract may comprise different constituents. Thus, in an embodiment the aqueous coffee extract constituents are selected from the group consisting of proteins, peptides and/or polyphenols from an aqueous coffee extract. Example 12 shows capsule formation using different coffee extract components.

As also mentioned for the process of the invention further aroma molecules may be loaded in the composition comprising coffee oil or directly in the coffee oil. Thus, in an embodiment the composition comprising coffee oil further comprises aroma constituents. In yet an embodiment the aroma constituents are derived from coffee. In another embodiment the composition comprising coffee oil is enriched in nutritional compounds. In yet an embodiment the nutritional compounds are selected from the group consisting of poly-unsaturated fatty acid, essential oils, fish oil, omega-3 fatty acids, omega-6 fatty acids, and/or oil soluble vitamins. As also described for the process according to the present invention, all constituents of the capsule may be derived from coffee beans. This includes both the solids and the oils.

The stability of the oil capsules according to the present invention can also be controlled by adjusting the concentrations of the starting materials. Thus, in an embodiment the capsule has an improved stability under mechanical agitation (e.g. stirring) of a dispersion of the same capsules. In another embodiment the capsule has an improved deformability under mechanically induced stress. In yet an embodiment the capsules have improved temperature stability. Thus, in an embodiment the capsules are stable at temperatures below 40° C., such as below 50° C., such as below 60° C., such as below 70° C., such as below 80° C. In the present context the wording "being stable at temperatures below a certain temperature" is to be understood as at least 50% of the oil capsules are stable for at least 1 minute at the specified temperature. In examples 2, 4 and 5 it is shown how the stability affected by stirring, temperature and visual inspection can be controlled/optimized by controlling the concentration of the input materials. One important feature of the capsules according to the present invention is that this membrane does not dissolve in aqueous phases in the classical pH range of coffee beverages (pH=4.0-8.0). Thus, in an embodiment the coffee capsules have improved pH stability.

The sizes of the capsule comprising coffee oil may also be controlled. Thus, in an embodiment the capsules according to the invention have a diameter in the range 1 µm to 1 mm, such as in the range 1-500 µm, such as in the range 1-100 µm, such as in the range 1-80 µm, such as in the range 1-50 µm, such as in the range 10-50 µm or such as in the range 10-20 µm.

The coffee oil capsules according to the present invention may be included in other compositions. Thus, an aspect of the present invention relates to a composition comprising coffee oil capsules according to the invention.

A further aspect according to the present invention relates to a food ingredient comprising a capsule comprising coffee oil according to the present invention. In an embodiment the food ingredient is selected from the group consisting of coffee powder, freeze dried coffee powder, beverages, coffee beverages, flavoured water, flavoured beverages, ice cream, soup, and frozen soup. In the present context "food ingredient" is to be understood as relating to both human and animal food/feed ingredients. Thus, the food ingredients according to the invention may find use in both human and animal food/feed.

Yet an aspect relates to a food product comprising a food ingredient according to the invention. In an embodiment the food product is selected from the group consisting of reconstituted coffee, ready to drink beverages, soups, bouillons, pet food, frozen soups, and ice cream.

The compositions according to the invention may also find use outside the food industry. Thus, in an embodiment the composition is a cosmetic, such as a skin lotion.

In a further aspect the invention relates to the use of a composition comprising coffee oil or derivatives thereof for the production of capsules comprising coffee oil. As shown in the examples coffee oil is essential for the formation of the capsules according to the invention.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Example 1

Production of Capsules Comprising Coffee Oil

The coffee oil capsules for controlled aroma release may be produced by using a microfluidics device. The schematic process is described in FIG. 1. Aromatized coffee oil and different coffee extracts (from green, roasted or toasted beans) are pumped into a microfluidic chip resulting in an oil-in-water emulsion. This emulsifying step is done at pH 6 and an interfacial membrane is formed later by the inline addition of coffee extract at pH>7, which results in a coffee oil capsule. The coffee oil capsule formed are concentrated and directly added to concentrated coffee extract (4-25° C.). The concentrated coffee extract containing coffee oil capsules is then frozen to −40° C. and then dried (e.g. by a freeze drying process).

In a more detailed example the coffee oil capsules were produced in the following way.

Materials and Methods

In a typical instant coffee manufacturing process, roasted ground beans are treated with water at elevated pressures and temperatures to extract soluble materials, with a simultaneous recovery of flavor condensates. Waste material remains in the form of slurry containing the insoluble spent coffee grounds with a moisture content of 75-80%. The slurry is then dewatered to a cake by screw presses. The resulting effluent can be separated into a crude oil (3% per effluent), aqueous and solid phases by centrifugation. The typical composition of the crude coffee oil is summarized the table 1. Most of the microscopy observations here after referred to in the examples were made on the capsules dispersions observed under a microscopy glass slide.

TABLE 1

Typical coffee oil compounds

| Typical Coffee Oil Constituents | Weight Percent |
|---|---|
| Triacylglycerols (TAG) | 65-80 |
| Diacylglycerols (DAG) | 2-5 |
| Monoacylglycerols (MAG) | <1 |
| Free Fatty Acids (FFA) | 4-7 |
| Sterols | <1 |
| Cafestol and Kahweol Esters | 12-18 |
| Cafestolene and Kahweolene Esters | 1-3 |
| Complex Lipids | 3-6 |
| Non-Lipids | 2-5 |
| Moisture | 0.2-2.1 |

Coffee oils obtained by the above process may be employed in the present invention.

Coffee oil capsules derived from green, toasted or roasted coffee and intermediates thereof were produced from different concentrations of coffee extract solution. The solutions were prepared from a freeze dried coffee powder.

The capsules may be observed with an approximately spherical shape on a solid substrate, e.g. a glass microscopy substrate: the oil contained in the capsule does not come in direct contact with the substrate, because the capsule membrane makes that impossible as long as the temperature is not raised significantly.

The solid material concentration in the final solution to attain a stable coffee oil capsule after process varied according to the material used.

Green coffee retentate UF: from 0.3-5%
Toasted coffee retentate MF: 0.5-2.5%
Roasted coffee retentate UF: 2.5%

It may though be possible to obtain capsules using 0.1-50% under other experimental settings.

The following procedure describes the formation of coffee oil capsules made of green coffee extract and coffee oil at final pH 7.

1. Green coffee extract was fractionated in a 0.2 μm membrane. The retentate obtained was filtrated with 30 kDa membrane and freeze-dried.
2. 2.5 g of this green coffee powder was dissolved in 97.5 g of water at room temperature for 15 min. Two solutions were prepared: 1) using water at pH value of about 5.0; 2) using water at pH value about 7.0-8.0.
3. An emulsion of aromatized coffee oil in water was prepared by using a microfluidics device. For instance a 5% o/w emulsion was prepared.
4. Green coffee solution at pH 7.0 was mixed into the emulsion. This mixture was done in line with via a cross-flow inlet stream in the outlet tube of the microfluidics channel.
5. The dispersion containing the oil capsules was added into concentrated coffee extract at 4° C.
6. The concentrated coffee extract/oil capsules mixture was frozen below −50° C.
7. The frozen concentrated coffee extract/oil capsules mixture was then dried by freeze-drying.

Depending on the trial, the oil capsules dispersion was concentrated in-line by gravitational forces just after step 4.

Example 2

Optimization of Production Process—Temperature Induced Bursting Test

Methods

Bursting tests of the coffee oil capsules were conducted by increasing the temperature a heating cell mounted on a Leica DMR microscope. The bursting process was recorded with the camera DC 300F coupled to the microscope by use of time-lapse sequence photography. The images were taken using the 5× or the 10× objectives.

Figure 2:
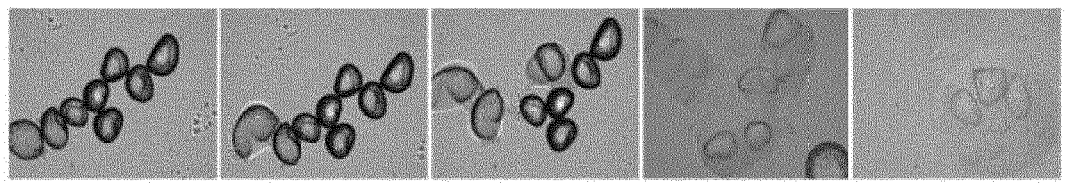
FIG. 2 shows temperature release profiles. A) 2.5% green coffee extract retentate MF (pH 9) in coffee extract. B) 2.5% green coffee extract retentate MF washed 6×UF (pH 6) in coffee.
Figure 2:
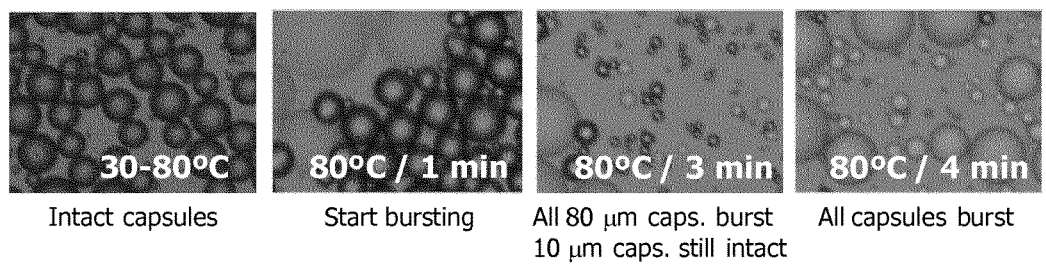

The heating profile applied was the following:
heating to 30° C.
Keeping at 30° C. during 1 minute
Heating to 80° C.
Keeping at 80° C. during 10 minutes
Cooling to room temperature Coffee oil capsules were produced according to the process in example 1 and the final coffee containing the oil capsules was poured onto a glass microscope slide. The sample was put into a heating cell unit and the temperature profile described above was applied while recording a video. By increasing the temperature the capsules membrane mechanical and barrier properties strongly decrease. If the capsules are observed in contact with a solid wall such as a glass plate (e.g. a microscopy slide), and the temperature is increased, an apparent burst of the capsules is observed, which thereby brings the oily core in direct contact with the aqueous phase by breakage of the membrane, while broken pieces of membrane were remaining stuck at the oil-water interface. Before breakage, the capsule is still clearly separated from the solid wall by its membrane. After burst, there is direct contact between the capsule oil and the wall, and between the oil and the aqueous phase. The decrease of the membrane mechanical properties upon temperature increase renders the capsule much more deformable and fragile compared to the capsules at room temperature. The exact temperature-time combination for the first capsule bursting and for the full sample bursting depended on the material the coffee oil capsules were made from. FIG. 2 show examples of capsule stability:

a) 2.5% green retentate MF pH 9 and coffee oil: Capsules started to burst at about 40° C. as can be seen by a rupture of the capsule membrane releasing the oil (different contrast in the image). Above 50° C. major part of capsules have already burst. Those capsules showed a brittle nature and were not very heat stable. The interfacial membrane material itself was not very sensitive to temperature, since some solid pieces could still be seen at 70° C. showing that it did not dissolve in the liquid phases.

b) 2.5% green retentate MF (filtered 6 times to remove e.g. citrate) pH 6 and coffee oil: Two sizes of capsules were produced having mean diameter of about 80 μm and 10 μm. The biggest capsules started bursting at 80° C./1 min and after 3 min all have burst. On the other hand, the smallest capsules started to burst after 3 min at 80° C. and 1 min later all have burst. Therefore, less deformable and smaller capsules are more stable.

Conclusion

Depending on the exact production process the temperature release profile may be controlled or strengthened to release the encapsulated coffee+aromas at a desired temperature range. Removal of acetic compounds increases the heat stability. Thus, one feature of the capsules according to the invention is their high resistance to mechanical stress, combined with their brittleness.

Example 3

Optimization of Production Process—Removal of Citrate

It is believed that citrate buffer may have negative effects on the formation and stability of the coffee oil capsules as also described in example 2. Thus, the aqueous coffee material was submitted to a filtering step for removing the citrate present in the powder. See also example 11.

Materials and Methods

Citrate was removed from coffee retentate according to the procedure:
1) Filtration unit was assembled with a membrane filter of 0.2 mm (for microfiltration) or 30 kDa pore sizes (for ultrafiltration) (FIG. 4).
2) 250 g of 2.5% coffee retentate solution at pH 7 was added.
3) The retentate was filtrated up to 6 times. At each time the sample volume was reduced from 250 mL to 80 mL (by measuring the permeate volume), then filled up again to 250 mL with $H_2O$. The applied pressure was about 6 bar.
   Membrane filter Tuffryn HT-200 0.2 µm Pall Life Science Ref No. T81660
   Membrane filter Omega 30 kDa 76 mm Pall Life Science Ref No. 87900A Results When using an aqueous composition comprising coffee without citrate it was possible to produce encapsulated oils at pH values as low as 6. Those coffee oil capsules were also of higher mechanical modulus and did not block the microfluidics junction, where the oil and the aqueous phase are in contact. Therefore, it may be possible to produce the encapsulated oils without having to change the pH as described in example 1. Furthermore, as described in example 2 more heat stable products may be obtained when citrate is removed.

Example 4

Optimization of Production Process—Visual Inspection

Figure 3:
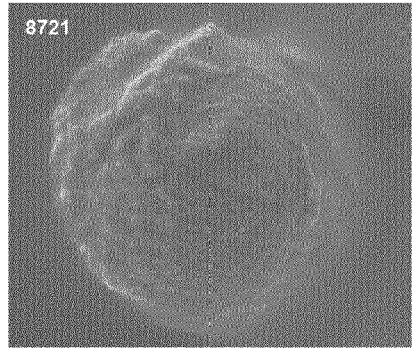
FIG. 3 shows SEM micrographs of 2.5% green coffee UF. A) SEM picture of pH 9 coffee oil capsules. Diameter around 80 μm. B) Cryo-SEM picture of pH 7 capsules. Diameter around 50 μm.
Figure 3:
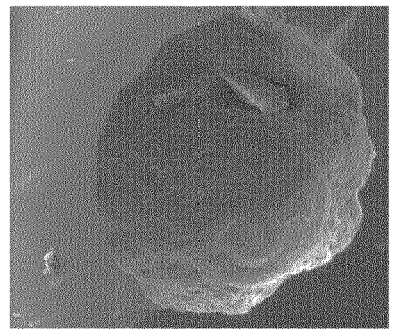

FIG. 3 shows coffee oil capsules produced by the above process using 2.5% green coffee. FIG. 4 shows an example of the coffee oil capsules obtained after steps 4 and 5 of the process. At pH 7, encapsulated oils were formed even at 0.1% green coffee retentate, but they burst very easy. After production some surface oil from encapsulated oils made with <0.5% or ≥5% coffee retentate was observed. In addition, those encapsulated oils seem to have a less rough surface. Thus, a concentration in the range 0.5-5% is preferred.

Example 5

Optimization of Production Process—Stirring Test

Figure 5:
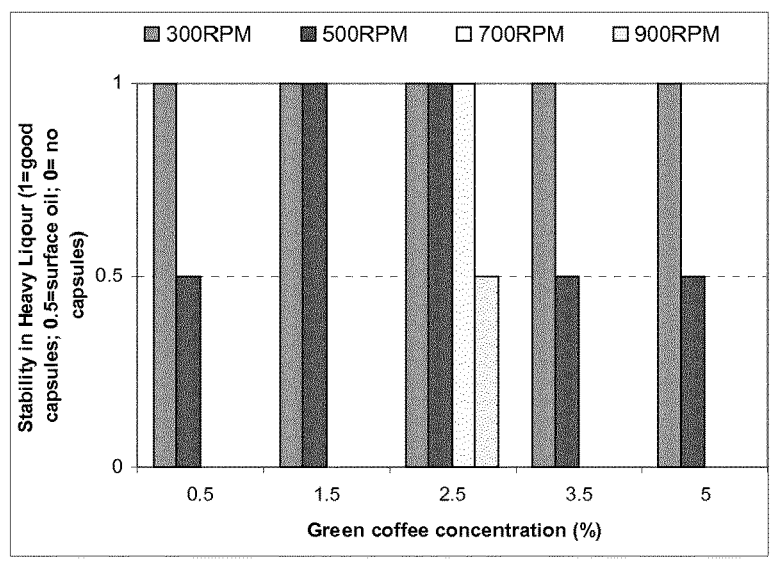
FIG. 5 shows stability of green coffee oil capsules, produced with several extract concentration, during incorporation into 50% concentrated coffee extract.

The effect of stirring during the incorporation step (step 5 in ex 4) was tested by adding the dispersion containing encapsulated oils (flow of 0.2 g/min) into 5 mL of concentrated coffee extract (2.4 cm diameter glass beaker). The stirring was performed at different rotational speeds (300-900 RPM) with a magnetic stirrer of 1.4 cm length. FIG. 5 shows that the encapsulated oils prepared with 2.5% green coffee extract UF were the most resistant, followed by coffee oil capsules made with 1.5% extract. The increase of coffee extract concentration beyond 2.5% led to capsules less resistant to mechanical stress during formation. FIG. 4 shows the microstructure of intact capsules after addition to concentrated coffee extract.

Example 6

Optimization of Production Process—Drying Process

Figure 6:
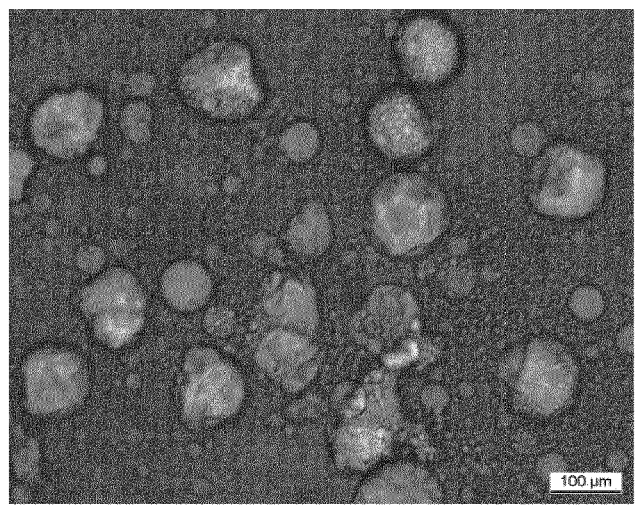
FIG. 6 shows intact coffee oil capsule after freeze-drying process in a coffee matrix.

FIG. 6 shows an example of the encapsulated oils obtained after step 7 in example 1 (freeze-drying). The freeze dried coffee powder comprising coffee oil capsules was dissolved on a microscope slide with water at room temperature and further observed using an optical microscope. FIG. 6 shows that several coffee oil capsules were still intact after freeze-drying process.

Example 7

Production of Green Toasted and Roasted Coffee Oil Capsules Oils—pH Effect

Figure 7:
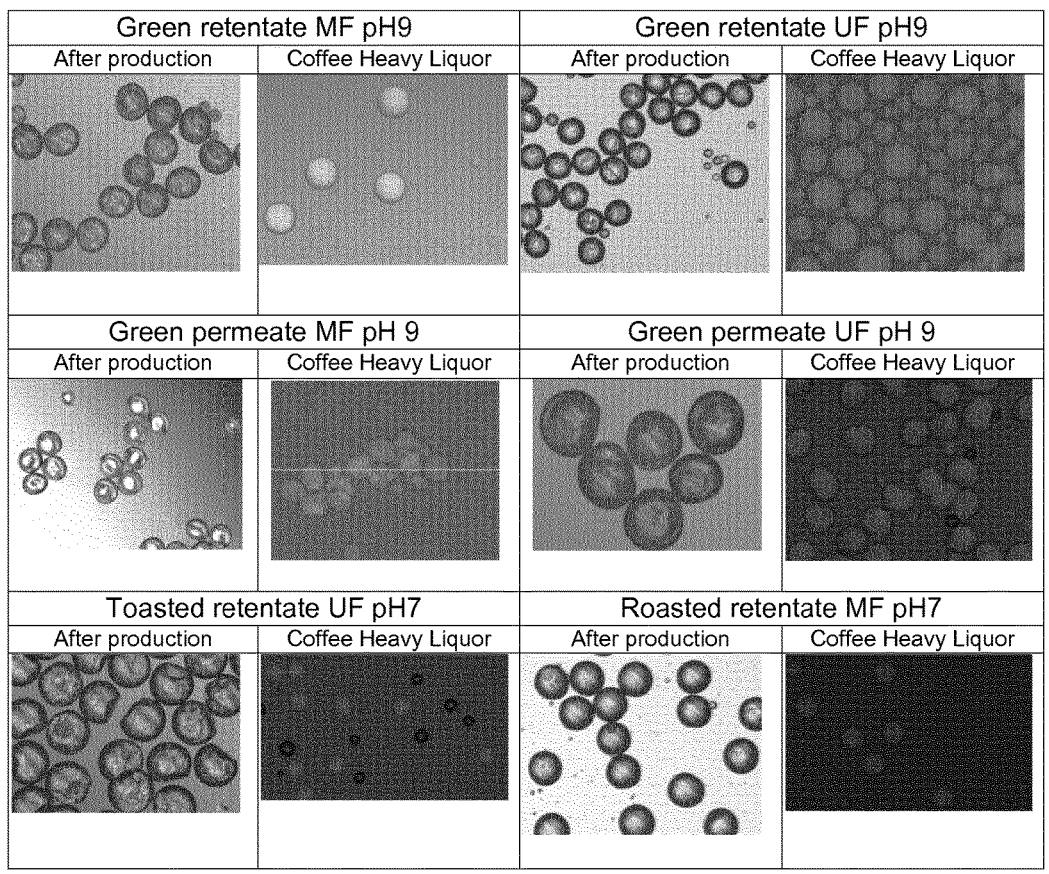
FIG. 7 shows microscopy pictures of green, toasted or roasted coffee oils capsules, pH 7-9, produced with 2.5% extract concentration as described in example 1. Pictures taken after production and in 50% concentrated coffee extract (coffee heavy liquor). MF: Microfiltration and UF: Ultrafiltration. The displayed coffee oil capsules have diameter in the range 50-150 μm.

FIG. 7 shows the microscopy pictures of coffee oil capsules produced with green, toasted or roasted at pH 7-9 after process steps 4 and 5 as described in example 1. The concentration of the extracts in all samples was fixed at 2.5% (w/w). The stability of the capsules right after processing was also dependent on the final pH of the dispersion.

Results and Conclusion
   Green coffee (pH 7-9): The higher the pH the higher was the stability of the capsules. For UF samples the microstructure at pH 9 shows that these capsules are more robust/brittle and less deformable, i.e. more resistant to mechanical stress without breaking.
   Toasted and Roasted coffee (pH 7-9): the coffee oil capsules at pH 7 were more stable, with higher mechanical resistance.

Weak capsules burst right after production (apparent burst observed at a solid wall or once in contact with air). It was possible to increase the mechanical stability of newly produced capsules by prolonging the contact time between the forming membrane, the coffee oil and the coffee extract, before any other step (e.g. contact with any other material than the coffee extract, drying, concentration, etc.).

Example 8

Production of Toasted and Roasted Coffee Oil Capsules—Concentration Effect

The best concentration range for forming coffee oil capsules from roasted and toasted coffee was evaluated at pH 7, since this was the pH value giving the most capsules at 2.5% coffee extract. A microfluidic chip was used to generate the capsules.

Results and Conclusion
   Toasted intermediate extract (MF): Coffee oil capsules could be formed at 2.5% coffee extract. However, oil leaking at the capsule surface was observed after production.
   Toasted final extract (UF): at 0.3% no capsules were formed. At 0.5% the capsules were so fragile that after 15 min in a beaker there was some leaked oil at the capsule surface. At 5%, oil leakage was immediately observed after production. Capsules formed with 2.5% extract were the most stable and could even be incorporated in 50% concentrated coffee extract (FIG. 7).
   Roasted intermediate extract (MF): at 0.3% no capsules were formed. At 0.5% the encapsulated oils were monodispersed, but quite a lot of surface oil was observed and after 10 min aging in the beaker nearly all capsules burst. Nevertheless, at 2.5% the capsules were stable enough to be incorporated in 50% concentrated coffee extract after some ageing time.

Roasted final extract (UF): At 0.5% no capsules were formed. At 2.5%, while collecting the capsules directly from a holding tube: rather weak capsules formed, not standing gently stirring conditions without breaking.

Conclusion

Overall the composition comprising coffee extract should preferably have a dry matter content by weight (w/w) of coffee extract in the range 0.5-5% during the process, such as 1-4%, such as 1-3%, such as 2-4%, or preferably around 2.5%.

Example 9

Coffee Oil Requirement for Formation of Membrane

Visual observation of formation or not of the interfacial membrane was used as a method to identify the type of oils that could be used for the formation of the coffee oil capsules. For that a drop of different oil types was made using a syringe in green coffee retentate aqueous phase.

The first observation made was that Medium Chain Triglycerides (MCT) or sunflower oil did not form the interfacial membrane, while coffee oils were clearly forming it. An important observation was that the interfacial membrane was formed with mixtures of coffee oil and MCT or sunflower. Table 2 shows that it is needed at least 40% of coffee oil mixed to MCT to form the interfacial membrane using the specific experimental parameters.

TABLE 2

Interfacial membrane formation with different oil mixes

| Coffee oil (%) | MCT oil (%) | Membrane* |
|---|---|---|
| 100 | — | ✓ |
| 40 | 60 | ✓ |
| 38 | 62 | X |
| — | 100 | X |

Example 10

Fractionating Coffee Oil

Visual observations have shown that mixing coffee oil to MCT or other oils also resulted in the formation of the membrane, while the MCT alone would not form this membrane (see example 9). Centrifugation of the coffee oil was performed to generate two different fractions of coffee oil. Therefore one could evaluate which oil fraction was rich in the compounds responsible for membrane formation.

Figure 8:
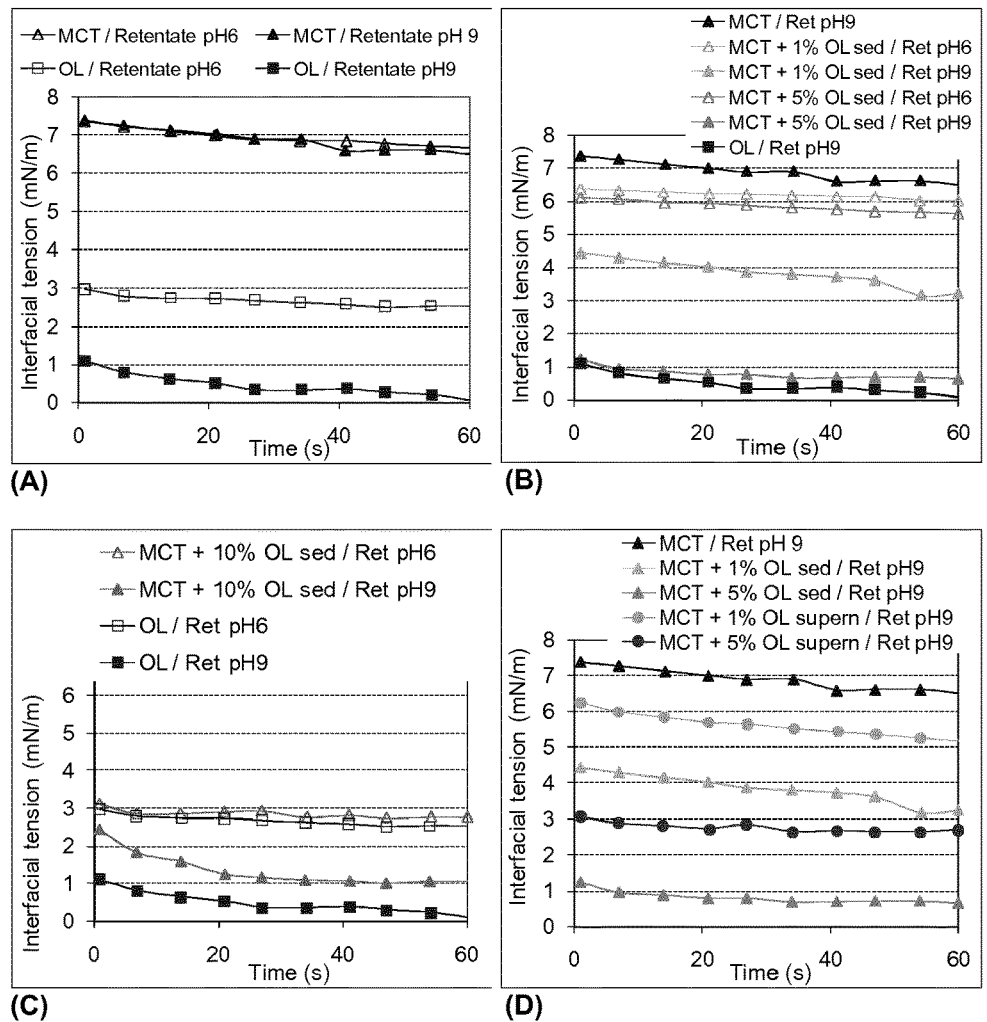
FIG. 8 shows interfacial tension between 2.5% green coffee retentate at different pH values and Medium Chain Triglyceride (MCT) mixed with surfactants from coffee oil.

The coffee oil sediments or supernatant obtained after centrifugation were added in different amounts to MCT. The water/oil interfacial tension of those mixtures was then measured as a function of time as described in FIG. 8.

FIG. 8A shows that the pH value of the aqueous phase does not reduce the interfacial tension when MCT is evaluated contrary to what was observed with pure coffee oil. However, the addition of small amount of oil sediment to MCT makes this water/oil interfacial tension susceptible to pH variation (FIGS. 8B and 8C). Up to 5% oil sediments the interfacial tension values at pH 6 did not changed as compared to pure MCT (FIG. 8B). However, at pH 9 the interfacial tension value decreased with the increase of the content of oil sediment in MCT. The addition of 10% coffee oil sediments in MCT caused the same interfacial response as pure coffee oil at both pH values 6 and 9 (FIG. 8C).

The coffee oil fraction of lighter density also contains some amount of surface active molecules, but in less concentration than the oil sediment. The addition of a certain amount of oil fraction of lighter density (e.g. 1% or 5%) to MCT causes less impact in the interfacial tension value than the same amount of sediment added to MCT (FIG. 8D). In summary, the reactive surfactants of coffee oil are concentrated in the coffee oil sediments.

Example 11

Citrate Effect on the Capsule Formation

As also described in examples 2 and 3, citrate influences formation of the capsules.

By analyzing the effect of citrate on membrane formation (Table 4) the hypothesis that citrate is competing for the surfactants seems pertinent.

TABLE 4

Effect of Na-citrate on membrane formation at different pH values.

| Concentration of Na-citrate | pH | Comments |
|---|---|---|
| 0.1M citr. in 2.5% green retentate | 7 | No membrane formed |
| 0.1M citr. in 2.5% green retentate | 9 | Very fine and weak membrane formed |
| ~0% citr. in 2.5% green retentate (sample after 6x filtration) | 6 | Very strong and elastic membrane formed |

If an oil droplet is injected in a coffee retentate solution containing 0.1M Na-citrate at pH 7, the membrane is not formed. By doing the same at pH 9, only a very fine and weak membrane was formed. Previously without the citrate, the membrane was formed at both pH values, being stronger at the alkaline pH. At pH 9, without citrate, the reactions to form the membrane are very fast (instantaneously), while at pH 7 the formation is slower.

The coffee retentate itself contains at least 0.8% of citric acid. Therefore, the aqueous phase was filtered six times in the lab, with water addition in between, to reduce to almost 0.0001% citrate content in the final retentate. This new retentate was tested for capsule formation. Results showed that not only was the capsules more elastic (microscopy evaluation) but also capsules could be formed at even lower pH values (minimum pH 6), which was not possible when using coffee retentate containing citrate (see also example 3).

Example 12

Process for Producing Encapsulated Oils—Requirement for Aqueous Phase

To verify the requirement for producing encapsulated oils in an oil-in-water emulsion different aqueous compositions were tested.

Materials and Methods

Figure 9:
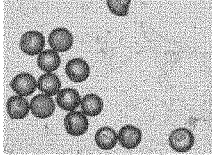
FIG. 9 shows capsules formed with a non-coffee aqueous phase and aromatized coffee oil.
Figure 9:
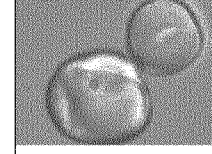
Figure 9:
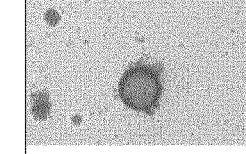
Figure 9:
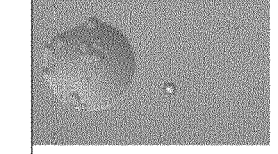

The concentration of the ingredients and the pH of the emulsions are listed below:

Na-caseinate: 1% protein at pH 7-9
Whey protein isolate (WPI) denatured: 2.5% at pH 7-9
Chlorogenic acid: 1% polyphenol at pH 9
Acacia gum: 2% polysaccharide at pH 7
Arabino galactan-protein: 0.5-2% polysaccharide-protein molecule at pH 7-9
Aqueous coffee extract
The process described in example 1 was used.
Results The results for Na-caseinate, Whey protein isolate (WPI) and Chlorogenic acid are shown in FIG. 9. Example from Aqueous coffee extract is shown in FIG. 7. Thus, in FIG. 9 it can be seen that encapsulated oils can be produced with proteins or polyphenols in the continuous (aqueous) phase. Similar results have been obtained using polysaccharides and proteins mixtures.

Example 13

Production of Encapsulated Fish Oil

The following procedure describes the formation of fish oil capsules.
1. Mix 2.5 g of Whey Protein Isolate (WPI) powder in 97.5 g of water at room temperature for 15 min.
2. Denature the protein by heating the solution at pH 5.8-7.2 for 80° C./30 min.
3. Centrifuge crude coffee oil at 50,000×g during 2 h and separate the gel phase (bottom phase).
4. Mix the fish oil with the gel phase to get 10% of gel in the oil and mix for 20 minutes until the gel is fully dispersed.
5. Prepare an emulsion of fish oil mix in water by using a microfluidics device. For the continuous phase a solution of denatured WPI pH 6.2 can be used. For instance a 5% o/w emulsion can be made.
6. Add the dispersion containing the capsules into skimmed milk at room temperature.

Just before step 6, the capsule dispersion can be concentrated in-line by gravitational forces.

Figure 10:
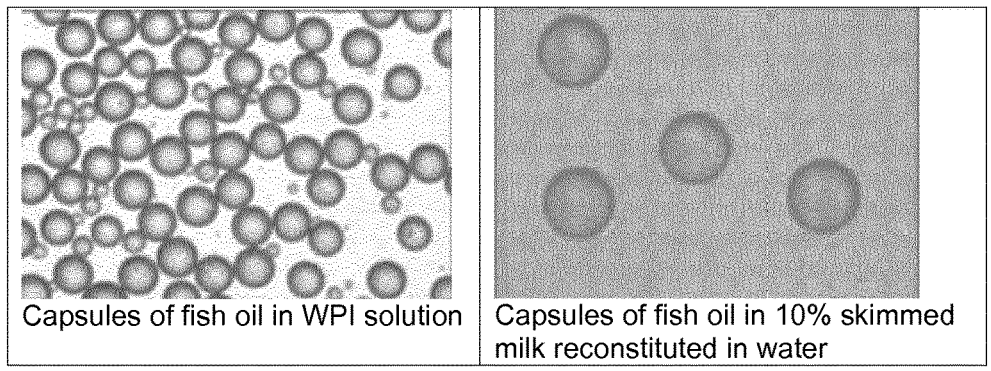
FIG. 10 shows fish oil capsules before and after addition to skimmed milk.

FIG. 10 shows the formed capsules before and after addition of skimmed milk.

As part of the dispersed phase, different oils can be used. However, under the specific experimental parameters it is necessary to mix them with at least 1% coffee crude oil gel sediment as described in Example 10.

The invention claimed is:

1. A process for producing a capsule comprising coffee oil, the process comprising:
    a) providing one or more aqueous compositions comprising coffee extract and a composition comprising coffee oil;
    b) mixing a first aqueous composition comprising coffee extract with the composition comprising coffee oil at a pH below 7 to provide an oil-in-water emulsion;
    c) raising the pH to a value in the range of 7 to 8; and
    d) providing the capsule comprising coffee oil.

2. The process according to claim 1, wherein the pH in step b) is in the range 4.0-6.5.

3. The process according to claim 1, wherein the pH during step c) is raised to the value in the range of pH 7 to 8 by addition of a second aqueous composition comprising coffee extract.

4. The process according to claim 1, wherein the first aqueous composition comprising coffee extract provided in step b) has a dry matter content by weight (w/w) of coffee extract in the range 0.1-50%.

5. The process according to claim 1, wherein the composition comprising coffee oil comprises at least 5% coffee oil by weight (w/w).

6. The process according to claim 1, wherein the coffee oil is a fraction of whole coffee oil.

7. The process according to claim 1, wherein 50-100% (w/w) of dry matter content of the capsule is derived from coffee beans.

8. A capsule comprising coffee oil, the capsule obtained by the process according to claim 1.

9. A capsule comprising coffee oil comprising
    a core of a composition comprising coffee oil; and
    a membrane surrounding the core, wherein the membrane comprises coffee oil constituents and aqueous coffee extract constituents.

10. The capsule comprising coffee oil according to claim 9, having a diameter in the range 1 μm to 1 mm.

11. A composition comprising a capsule comprising coffee oil comprising:
    a core of a composition comprising coffee oil; and
    a membrane surrounding the core, wherein the membrane comprises coffee oil constituents and aqueous coffee extract constituents.

12. A food ingredient comprising a capsule comprising coffee oil comprising:
    a core of a composition comprising coffee oil; and
    a membrane surrounding the core, wherein the membrane comprises coffee oil constituents and aqueous coffee extract constituents.

13. The composition according to claim 11, wherein the composition is selected from the group consisting of a cosmetic, a skin lotion, a pharmaceutical composition, a nutritional food composition, a nutraceutical, and a medicament.

14. A process for producing a capsule comprising coffee oil, the process comprising:
    a) providing one or more aqueous compositions comprising coffee extract and a composition comprising coffee oil;
    b) emulsifying the composition comprising coffee oil with an aqueous phase to provide a first oil-in-water emulsion;
    c) mixing a first aqueous composition comprising coffee extract with the first oil-in-water emulsion at a pH below 7 to provide a second oil-in-water emulsion;
    d) raising the pH to a value in the range of 7 to 8;
    e) concentrating the second oil-in-water emulsion;
    f) mixing the second oil-in-water emulsion with coffee extract;
    g) drying the second oil-in-water emulsion; and
    h) providing the capsule comprising coffee oil.

15. The process according to claim 3, wherein the second aqueous composition consists of water and components derived entirely of coffee constituents.

16. The process according to 1, wherein the one or more aqueous compositions comprising coffee extract are free of citrate and acetic compounds.

17. The process according to 14, wherein the one or more aqueous compositions comprising coffee extract are free of citrate and acetic compounds.

18. The process according to 1, wherein the capsule consists of water and components derived entirely from coffee.

19. The process according to 14, wherein the entirety of the capsule comprising coffee oil is derived from coffee.

20. The process according to claim 3, wherein the pH during step c) is raised to the value in the range of 7 to 8 by the coffee extract in the second aqueous composition.

* * * * *